US009149042B2

United States Patent
Puigvert Colomer et al.

(10) Patent No.: US 9,149,042 B2
(45) Date of Patent: Oct. 6, 2015

(54) ANTISEPTIC SOLUTION OF DI(4-CHLORO-PHENYLDIGUANIDO) COMPOUND AND PROCESS THEREFOR

(75) Inventors: Marina Puigvert Colomer, Barcelona (ES); Sergio Lloret Perez, Barcelona (ES)

(73) Assignee: Medichem, S.A., Sant Joan Despi (ES)

( * ) Notice: Subject to any disclaimer, the term of this patent is extended or adjusted under 35 U.S.C. 154(b) by 119 days.

(21) Appl. No.: 13/420,250

(22) Filed: Mar. 14, 2012

(65) Prior Publication Data

US 2012/0238635 A1 Sep. 20, 2012

Related U.S. Application Data

(63) Continuation-in-part of application No. 13/211,846, filed on Aug. 17, 2011.

(60) Provisional application No. 61/500,969, filed on Jun. 24, 2011.

(30) Foreign Application Priority Data

| Mar. 14, 2011 | (EP) | 11382069 |
| Jun. 20, 2011 | (ES) | 201131038 |
| Mar. 10, 2012 | (EP) | 12158959 |

(51) Int. Cl.
| *A01N 47/44* | (2006.01) |
| *A61K 9/08* | (2006.01) |
| *A61K 31/045* | (2006.01) |
| *A61K 31/155* | (2006.01) |

(52) U.S. Cl.
CPC . *A01N 47/44* (2013.01); *A61K 9/08* (2013.01); *A61K 31/045* (2013.01); *A61K 31/155* (2013.01)

(58) Field of Classification Search
CPC ....... A01N 47/44; A01N 25/00; A01N 25/02; A01N 25/22; A01N 2300/00; A61K 2300/00; A61K 31/00; A61K 31/13; A61K 31/045; A61K 9/08; A61K 31/155
USPC ................... 424/405; 514/635, 724
See application file for complete search history.

(56) References Cited

U.S. PATENT DOCUMENTS

| 4,548,807 A | 10/1985 | Westfall et al. | |
| 2004/0179889 A1 | 9/2004 | Tufts et al. | |
| 2006/0094777 A1* | 5/2006 | Westfall | 514/494 |
| 2007/0254854 A1* | 11/2007 | Magallon et al. | 514/150 |

FOREIGN PATENT DOCUMENTS

| CN | 101 336 910 A | * | 1/2009 |
| EP | 1 044 686 A1 | * | 10/2000 |
| EP | 2 499 913 A1 | | 9/2012 |
| EP | 2 499 914 A1 | | 9/2012 |
| ES | 2 332 978 A1 | | 2/2010 |
| WO | WO 2007/130981 A2 | | 11/2007 |
| WO | WO 2007/130982 A2 | | 11/2007 |

OTHER PUBLICATIONS

ChloraPrep® with Tint, Feb. 2010 (obtained on the internet at http://www.ivteam.com/iv_skin_prep/ChloraPrep_with_Tint_SmPC.pdf on Jun. 25, 2012).*
Medi-Flex and FDA Meeting Jun. 16, 2004 Proposed Meeting Agenda, Minutes of Meeting and Slides (obtained on the internet at http://www.fda.gov/ohrms/dockets/dockets/05p0458/05p-0458-1st0001.pdf, http://www.fda.gov/ohrms/dockets/dockets/05p0458/05p-0458-mm0001.pdf and http://www.fda.gov/ohrms/dockets/dockets/05p0458/05p-0458-ts00001.pdf on Jun. 26, 2012).*
Hibiclens, Physician's Desk Reference, 2001, p. 628.*
Debra Faye Duxbury, "The Photochemistry and Photophysics of Triphenylmethane Dyes in Solid and Liquid Media", Chemical Reviews, 1993, 93(1), 381-433.*

* cited by examiner

*Primary Examiner* — John Pak
*Assistant Examiner* — Nathan W Schlientz
(74) *Attorney, Agent, or Firm* — Leydig, Voit & Mayer, Ltd.

(57) ABSTRACT

The present invention relates to a stable antiseptic solution comprising: a di(4-chlorophenyldiguanido) compound or a pharmaceutically acceptable salt thereof, wherein said di(4-chlorophenyldiguanido) compound or a pharmaceutically acceptable salt thereof is a compound of formula (I) or a pharmaceutically acceptable salt thereof. The invention further relates to a process for preparing said antiseptic solution.

9 Claims, No Drawings

ANTISEPTIC SOLUTION OF DI(4-CHLORO-PHENYLDIGUANIDO) COMPOUND AND PROCESS THEREFOR

CROSS-REFERENCE TO RELATED APPLICATION

This patent application claims the benefit of European Patent Application No. EP 11382069.0 filed on Mar. 14, 2011, Spanish Patent Application No. ES 201131038 filed on Jun. 20, 2011, European Patent Application No. EP 12158959.2 filed on Mar. 10, 2012, and U.S. Provisional Patent Application No. 61/500,969, filed Jun. 24, 2011, each of which is incorporated by reference. This patent application is a continuation-in-part of U.S. patent application Ser. No. 13/211,846 filed on Aug. 17, 2011, which is incorporated by reference.

BACKGROUND OF THE INVENTION

Chlorhexidine is the international common accepted name for N,N-bis(4-chlorophenyl)-3,12-diimino-2,4,11,13-tetraazatetradecanediimidamide (also known as 1,6-di(4"-chlorophenyldiguanido)hexane), and has an empirical formula of $C_{22}H_{30}Cl_2N_{10}$, a molecular weight of 505.45 g/mol, and a chemical structure of formula (I):

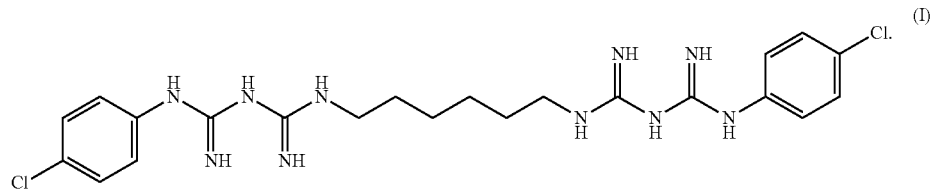 [SMILES: N=C(NCCCCCCNC(=N)NC(=N)Nc1ccc(Cl)cc1)NC(=N)Nc1ccc(Cl)cc1]

Chlorhexidine is a well-known topical antiseptic and disinfectant that has been used for more than 30 years. Products comprising chlorhexidine are used for a number of applications such as, for example, daily hygiene application, oral antiseptic applications, hand and skin disinfection, and general disinfection (e.g., equipment, surfaces and textiles). Chlorhexidine is a highly active bactericidal agent having a broad activity with low levels of toxicity and strong skin binding properties. Chlorhexidine is primarily bactericidal against gram-positive and gram-negative bacteria, and its activity extends to yeasts, including *Candida albicans*. The bactericidal activity of chlorhexidine differs from that observed with povidone-iodine or 70% isopropyl alcohol. For example, chlorhexidine has demonstrated an immediate bactericidal effect as well as a cumulative effect that persists for hours and even days after it is applied, and unlike iodophors, the germicidal activity of chlorhexidine has shown statistically significant efficacy in reducing bacterial counts in the presence of blood and other protein-rich biomaterials.

Chlorhexidine is often applied preoperatively to disinfect materials and surfaces or skin of a patient prior to surgery. An important consideration for the user is the appearance of a chlorhexidine solution. For example, upon visual inspection, the user needs to be able to determine that a) the antiseptic solution has been applied, and b) where the antiseptic solution has been applied. However, chlorhexidine by itself forms clear, colorless solutions which makes it difficult for the user to make such a determination. Thus, it is desirable to use colored chlorhexidine solutions.

Numerous problems are encountered when color additives (e.g., tints or dyes) are added to an antiseptic solution of chlorhexidine in amount sufficient to stain a patient's skin or surgical field before surgery. The tint or dye can react with chlorhexidine to form a precipitate, which can lead to non-uniform distribution of the colored antiseptic solution upon its application. In addition, the coloring additive can react with chlorhexidine to form impurities thereby partially inactivating the chlorhexidine solution and increasing the impurity profile of the antiseptic solution. In addition, the chemical stability of the product is lessened resulting in a shortened shelf life.

The development of colored solutions of chlorhexidine, with a sufficient shelf life has proven to be difficult. Moreover, the development of colored solutions of chlorhexidine, advantageously prepared by efficient formulation processes has proved problematic.

U.S. 2004/0179889 ("the '889 publication") acknowledges the problems associated with colored chlorhexidine solutions. The '889 publication purportedly describes that the problems can be alleviated by using a specific, specialized applicator for applying chlorhexidine solution. The disclosed applicator comprises at least one ampoule formed of a frangible material and adapted to contain liquid to be applied; at least one hollow body defining an internal chamber adapted to receive at least one ampoule; and at least one porous element that contains colorant, wherein the porous element is positioned such that liquid flows through the porous element when at least one ampoule is fractured and colorant is transferred to the liquid to be applied.

The use of specific applicators to administer antiseptic solution or to reconstitute the solution prior to its use, is inconvenient and is not feasible for some applications.

WO 2007/130981 ("the '981 publication") supposedly discloses a solution of chlorhexidine together with cationic dye in an amount sufficient to stain patient's skin. It is believed that since chlorhexidine pharmaceutically acceptable salts are cationic compounds, they are compatible with other cationic and non ionic substances, but are chemically incompatible with anionic compounds.

The use of cationic dyes, as well as products comprising cationic dyes, can pose a health hazard. Numerous disadvantages are related to using cationic dyes in antiseptic formulations, including adverse toxicological and carcinogenic effects. Reports of hypersensitivity and hyperkinetic activity, especially among children, add to concerns over the safety of using cationic dyes in products.

Moreover, the '981 publication describes that an anionic dye may be used provided that the antiseptic solution also comprises a cationic excipient. The '981 publication also describes that anionic dyes, including FD&C dyes, form a precipitate with chlorhexidine, even at very low concentrations. The precipitate forms as an insoluble salt of a chlorhexidine cation and at least one dye anion. As such, adding an anionic dye alone to an aqueous chlorhexidine solution removes a significant fraction of the chlorhexidine from solution, thereby decreasing the efficacy of the solution.

WO 2007/130982 ("the '982 publication") attempts to solve the above described problems by providing solutions of chlorhexidine together with an anionic dye and a cationic excipient (e.g., cationic detergents, surfactants or excipients containing quaternary nitrogen. The '982 publication describes the use of a cationic excipient together with an anionic excipient is essential and that as the negative charge of an anionic dye is "hidden" from the chlorhexidine by a cationic excipient, the chlorhexidine-dye salt will not immediately form.

However, using additional excipients in antiseptic solution, especially cationic excipients may cause dangerous adverse affects related with allergies, intolerance and/or irritation.

In addition, according to the Summary of Product Characteristics for CHLORAPREP® 2% (w/v)/70% (v/v) cutaneous solution, chlorhexidine is incompatible with anionic agents (e.g., http://www.medicines.org.uk/emc/medicine/22302/SPC/chloraprep/).

The disclosure of each of the '889 publication, the '981 publication, the '982 publication, and the Summary of Product Characteristics for CHLORAPREP® are incorporated herein by reference.

In view of the foregoing, there is a need to provide colored antiseptic solutions comprising chlorhexidine which are safe, have improved properties and good chemical stability. There is also a need for colored antiseptic chlorhexidine solutions which can be prepared by efficient formulation processes.

BRIEF SUMMARY OF THE INVENTION

The present invention provides colored, stable antiseptic solution comprising a di(4-chlorophenyldiguanido) compound of formula (I) or a pharmaceutically acceptable salt thereof, ingly, the antiseptic solutions of the invention is not contraindicated in patients having a hypersensitivity to cationic excipients or cationic dyes. Moreover, the substantial absence of cationic excipients reduces the absorption of isopropyl alcohol or chlorhexidine through skin. Since there is a little percutaneous absorption of the antiseptic solution of the invention it is indicated, for example, for use on pre-injection sites.

The invention also provides a process for preparing colored, stable antiseptic solution comprising a di(4-chlorophenyldiguanido) compound of formula (I) or a pharmaceutically acceptable salt thereof.

DETAILED DESCRIPTION OF THE INVENTION

The present invention provides colored, stable antiseptic solutions comprising a di(4-chlorophenyldiguanido) compound of formula (I), or a pharmaceutically acceptable salt thereof

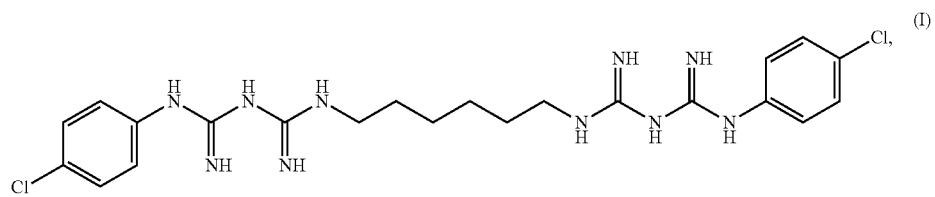 [SMILES: N=C(NCCCCCCNC(=N)NC(=N)Nc1ccc(Cl)cc1)NC(=N)Nc1ccc(Cl)cc1]

wherein the antiseptic solution is essentially free of cationic excipients.

In an embodiment, the invention provides a stable antiseptic solution comprising, consisting essentially of, or consisting of a di(4-chlorophenyldiguanido) compound of formula (I) or a pharmaceutically acceptable salt thereof, one or more anionic dyes, and one or more solvents.

Without wishing to be bound to a particular theory, it is believed that the antiseptic solution of the invention exerts its biological effects upon bacterial cells through nonspecific interactions with acidic phospholipids of the cell membranes. The antiseptic solution of the invention is both an excellent antiseptic and disinfectant. Although the antiseptic solution of the invention is more effective against gram-positive bacteria, the antiseptic solutions of the invention exhibit bactericidal or bacteriostatic activity against a wide range of gram-positive and gram-negative bacteria. The antiseptic solutions of the invention also exhibit some activity against certain

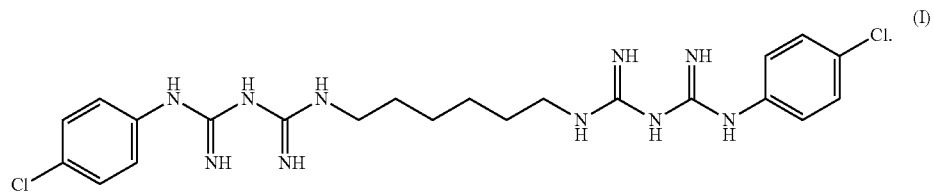 [SMILES: N=C(NCCCCCCNC(=N)NC(=N)Nc1ccc(Cl)cc1)NC(=N)Nc1ccc(Cl)cc1]

The antiseptic solution of the invention is suitable for disinfecting the skin or surgical field prior to invasive medical procedures, and the antiseptic solution of the invention has good pharmacokinetic properties, including a rapid onset of action and long lasting activity against pathogens.

The stable antiseptic solution of the invention exhibits a high stability and excellent compatibility with anionic dyes, even being substantially free of cationic excipients. Accordspecies of *Pseudomonas* and *Proteus*, as well as some viruses and fungi. It is believed that the combination of solvents (e.g., isopropyl alcohol and water) used to prepare the antiseptic solutions of the invention can enhance both efficacy and stability of the antiseptic solutions.

In accordance with the invention, the antiseptic solution is essentially free or substantially free of cationic excipients. Applicants have found that antiseptic solutions comprising chlorhexidine or a pharmaceutically acceptable salt thereof, one or more anionic dyes, and one or more solvents exhibit good chemical and physical stability even though said solutions are essentially free of cationic excipients. Typically, the antiseptic solution of the invention comprises less than about 0.01 wt %, preferably less than about 0.001 wt % of the cationic excipient. In a preferred embodiment the antiseptic solution does not comprise any cationic excipient or only in amounts under the detection limit. In a particularly preferred embodiment, the antiseptic solution of the invention is free of any cationic excipients.

In accordance with the invention, the antiseptic solution of the invention comprises one or more anionic dyes. Although others have reported adding colorants to di(4-chlorophenyl-diguanido) compound of formula (I), numerous problems are encountered with an increased amount of colorants. However, it is believed that applicants are the first to report the addition of anionic dye in amount sufficient to stain or color, without the need of further additional excipients to provide an antiseptic solution of chlorhexidine which does not precipitate and is chemically stable during shelf life.

Applicants have surprisingly discovered that antiseptic solutions of a di(4-chlorophenyldiguanido) compound of formula (I) or a pharmaceutically acceptable salt thereof can be prepared wherein the solution comprises one or more anionic dyes even though the antiseptic solution is essentially free of cationic excipients. Without wishing to be bound to a particular theory, it is proposed that the inclusion of one or more anionic dyes into the antiseptic solution of the present invention can prevent precipitation and can assure chemical stability and shelf life of the antiseptic solutions. For example, antiseptic solutions of the invention are stable for at least about 3 months, at least about 6 months, at least about 12 months, and even at least about 18 months. Moreover, the antiseptic solution of the present invention is stable in relative extreme hot or cold temperature conditions.

As used herein, the term "antiseptic solution" refers to any liquid which comprises said di(4-chlorophenyldiguanido) compound of formula (I) (i.e., chlorhexidine) or a pharmaceutically acceptable salt thereof wherein all the components are completely dissolved and said solution is ready for administration. Further, the antiseptic solution does not require either any further preparation (e.g., reconstitution) prior to administration, or any specialized applicator. The antiseptic solution of the invention is suitable as an antibacterial and/or disinfectant solution for skin disinfection; handwashing; oral care; irrigation of surgical wounds, the urinary bladder or vagina; topical treatment of burn wounds; for treatment of peritonitis in peritoneal dialysis; and/or for all the purposes related to its antiseptic and/or disinfectant properties to prevent infections such a nosocomial infection, surgical-site infections, catheter-related infections, surgical wound infections, oral infections.

As used herein, the term "stable" refers to a solution that after about 24 hours, preferably after about 96 hours, more preferably after about 1 month, most preferred after about 3 months is clear and leaves no residual solids visible to the human eye. Moreover, the stable antiseptic solution of the invention is clear and does not leave residual solids visible to the human eye after a stability test in the conditions of 25±2° C. and 60%±5% relative humidity during at least about 3 months. Even more preferably after a stability test in the conditions: 25±2° C. and 60%±5% relative humidity, during at least about 3 months, preferably at least about 6 months, even more preferably during at least about 12 months and the most preferably during at least about 18 months the solution of the invention is clear, leaves no residual solids visible to the human eye and is chemically stable, i.e., contains insubstantial amount of p-chloroaniline impurity, preferably less than 0.25% (w/w), after undergoing the stability test mentioned above.

As used herein, the term "anionic dye" refers to any colored substance, for example, those containing auxochromes, and thus capable of coloring substances to which they are applied or incorporated. Such colorants are used, for example, for staining and coloring, as a test reagent, and as a therapeutic agent. Anionic dyes are characterized that they have a negative charge and attach to cationic surfaces. Anionic dyes include many compounds from various classes of dyes having differences in structure (e.g., azoic, anthraquinone, triphenylmethane and nitro dyes) but possess ionic substituents as a common, water-solubilizing feature.

As used herein, the term "cationic excipient" refers to the cationic excipient as disclosed in the WO 2007/130982. Cationic dyes are also considered as cationic excipients in the context of the present invention.

As used herein, the term "essentially free" refers to an insubstantial amount, for example, when describing an amount of cationic excipient, essentially free refers to less than 0.01% by weight of cationic excipient, or even less than 0.001% by weight of cationic excipient. Preferably the antiseptic solution is free of any cationic excipients.

As used herein, the term "insubstantial" amount of p-chloroaniline impurity means preferably less than approximately 0.25% (w/w) (i.e., not more than 0.25%; NMT 0.25%) after the above mentioned stability test. The stability studies are preferably carried out as defined in ICH Topic Q1A "Stability Testing of New Drug Substances and Products" (CPMP/ICH/2736/99), the disclosure of which is incorporated herein by reference.

As used herein, the term "about" when used in the present invention preceding a number and referring to it, is meant to designate any value which lies within the range defined by the number ±10% of its value, preferably a range defined by the number ±5%, more preferably range defined by the number ±2%, still more preferably a range defined by the number ±1%. For example "about 10" should be construed as meaning within the range of 9 to 11, preferably within the range of 9.5 to 10.5, more preferably within the range of 9.8 to 10.2, and still more preferably within the range of 9.9 to 10.1.

As used herein, the term "surgical field" refers to a sterile, isolated area of the operative field, where surgery is performed, including but not limited to the patient and surfaces surrounding the patient (e.g., operating table and surgical equipment).

As used herein, the terms "lower alcohol" or "lower alkanol" refer to straight chain or branched alkyl residues containing 1 to 8 carbon atoms with at least one hydroxy group, such as methanol, ethanol, propanol, n-propanol, isopropanol, butanol, n-butanol, 1-butanol, 2-butanol, tert-butanol, pentanol and the like.

As used herein, precipitation and/or particulate contamination refer to the formation of any solids in the antiseptic solution of the invention or the particulate contamination that consists of extraneous, mobile, undissolved particles, other than gas bubbles, unintentionally present in the solution. Precipitation or particulate contamination can be measured, for example, by any suitable tests that provide an assessment of the quality of the solution comprising di(4-chlorophenyldiguanido) compound of formula (I) or pharmaceutically acceptable salt thereof and an anionic dye in an amount sufficient to stain a patient's skin or surgical field before surgery. An illustrative test is a visual assessment for visible particles. For example, precipitation and/or particulate contamination of the antiseptic solution of the invention can be measured by first removing any adherent labels from the container and washing and drying the outside of the container, if the container is transparent. If the container is not transparent the antiseptic solution can be placed in previously washed and dried transparent container. Further, the container might be gently swirled or inverted, ensuring that air bubbles are not introduced, and then the contents of the container should be observed. It is desirable that no particulate contamination is observed. One skilled in the art will recognize that other test methods are suitable.

As used herein, the chemical stability during shelf life refers to the antiseptic solution of the invention having a desirable impurity profile as described herein. Typical impurities include, for example, p-chloroaniline and visible particles. Desirably, the antiseptic solution of the invention has a low level of impurities and is stable over a period of time (e.g., 3 months, 6 months, 12 months, and/or 18 months). For example, desirably the antiseptic solution of the invention has and maintains a level of p-chloroaniline that is not more than 0.25% upon storage for 3 months at either room temperature (e.g., 20-25° C.) or at about 40° C. Further, it is desirable that the colored, antiseptic solution of the invention remains free of visible particles upon storage and during use. Any suitable method known to one of ordinary skill can be used to test for impurities. In a preferred embodiment, a method to measure p-chloroaniline impurity is an HPLC method, based on USP33 references and ICH guidelines requirements.

In keeping with the invention, the antiseptic solution of the invention comprises one or more anionic dyes. Suitable anionic dyes that may be employed within antiseptic solution of the present invention include, but are not limited to, FD&C dyes, such as, for example, FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), Food Red 3 (Carmoisine), FD&C Yellow No. 5 (Tartrazine), and FD&C Yellow No. 6 (Sunset Yellow FCF). Preferably, the antiseptic solution of the present invention comprises FD&C Red No. 40 (Allura Red) anionic dye. In an embodiment, the one or more anionic dyes of the antiseptic solution is selected from the group consisting of FD&C Blue No. 1, FD&C Blue No. 2, FD&C Green No. 3, FD&C Red 40, Food Red 3 (Carmoisine), FD&C Yellow No. 5, and FD&C Yellow No. 6, and mixtures thereof. These anionic dyes are also known as: FD&C Blue No. 1, CAS 3844-45-9, Blue FCF, Acid Blue 9, Alzen Food Blue No. 1, Atracid Blue FG, Erioglaucine, Eriosky blue, Patent Blue AR, Xylene Blue VSG, FD&C Blue No. 2, CAS 860-22-0, Indigo carmine, 3,3'-dioxo-2,2'-bis-indolyden-5,5'-disulfonic acid disodium salt, indigotine, 5,5'-indigodisulfonic acid sodium salt FD&C Green No. 3, CAS 2353-45-9, Fast Green FCF, Food green 3, Green 1724, Solid Green FCF, C.I. 42053, ethyl-[4-[[4-[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium, FD&C Red No. 3, CAS 16423-68-0, erythrosine, 2-(6-hydroxy-2,4,5,7-tetraiodo-3-oxo-xanthen-9-yl)benzoic acid, FD&C Red No. 40, CAS 25956-17-6, Allura Red, Food Red 17, C.I. 16035, E129, 2-naphthalenesulfonic acid disodium salt, disodium 6-hydroxy-5-((2-methoxy-5-methyl-4-sulfophenyl)azo)-2-naphthalenesulfonate Food Red 3: CAS 3567-69-9, azorubine, carmoisine, disodium 4-hydroxy-2-[(E)-(4-sulfonato-1-naphthyl)diazenyl]naphthalene-1-sulfonate FD&C Yellow No. 5, CAS 1934-21-0, tartrazine, trisodium (4E)-5-oxo-1-(4-sulfonatophenyl)-4-[(4-sulfonatophenyphydrazono]-3-pyrazolecarboxylate FD&C Yellow No. 6, CAS 2783-94-0, Orange Yellow S, FD&C Yellow 6, C.I. 15985, E110, disodium 6-hydroxy-5-[(4-sulfophenyl)azo]-2-naphthalenesulfononate.

In a particularly preferred embodiment, the antiseptic solution comprises one anionic dye.

The antiseptic solutions of the invention comprise a suitable amount of anionic dye. Typically, the antiseptic solutions comprise an amount of anionic dye sufficient to stain a patient's skin or surgical field when applied before surgery. For example, the one or more anionic dyes typically is present in the antiseptic solution of the invention in an amount less than about 5% (w/v) of the solution and preferably less than about 1% (w/v) of the solution, preferably less than about 0.5% (w/v) of the solution, preferably less than about 0.3% (w/v) of the solution. Typical ranges can include about 0.05% to about 1.0% w/v, or more preferably about 0.10% to about 0.60% w/v. In a particular embodiment of the present invention as herein described, the concentration of anionic dye is about 0.2% (w/v) of the solution. In certain particularly preferred embodiments of the invention, however, it is further preferred that the concentration of anionic dye is even lower, and for example is in the range of about 0.01% (w/v) to about 0.1% (w/v) of the solution, more preferably in the range of about 0.01% (w/v) to about 0.04% (w/v) of the solution and even more preferably in the range of about 0.02% (w/v) to about 0.03% (w/v) of the solution. Most preferably in such embodiments of the invention, the concentration of anionic dye is about 0.025% (w/v) of the solution.

In keeping with an aspect of the invention, the antiseptic solution of the invention can comprise a pharmaceutically acceptable salt of the di(4-chlorophenyldiguanido) compound of formula (I). A pharmaceutically acceptable salt of chlorhexidine typically is used to help with solubility. In a preferred embodiment, the antiseptic solution of the invention comprises at least one pharmaceutically acceptable salt of di(4-chlorophenyldiguanido) compound of formula (I). Suitable pharmaceutically acceptable salts of the di(4-chlorophenyldiguanido) compound of formula (I) include the gluconate, acetate, chloride, bromide, nitrate, sulfate, carbonate, and phosphanilate salts, and mixtures thereof. In a particularly preferred embodiment, the pharmaceutically acceptable salt is the gluconate salt of di(4-chlorophenyldiguanido) compound of formula (I), that is chlorhexidine gluconate.

One skilled in the art will recognize that chlorhexidine can form bivalent salts (e.g. chlorhexidine digluconate).

The concentration of di(4-chlorophenyldiguanido) compound of formula (I) or its pharmaceutically acceptable salt in the antiseptic solution of the invention can vary within various embodiments of the present invention. In a preferred embodiment, the di(4-chlorophenyldiguanido) compound of formula (I) or its pharmaceutically acceptable salt is present in an amount of about 0.1% (w/v) to about 10% (w/v) of the solution. Preferably, the concentration of di(4-chlorophenyldiguanido) compound of formula (I) or its pharmaceutically acceptable salt in the antiseptic solution of the present invention is in the range of about 0.5% to about 4% (w/v) of the solution, more preferably in the range of about 1% to about 3% (w/v) and still more preferably in the range of about 1.5% to about 2.5% (w/v). Even more preferably, the antiseptic solution of the present invention comprises about 2% (w/v) of the di(4-chlorophenyldiguanido) compound of formula (I) or pharmaceutically acceptable salt thereof.

It is desirable that the one or more solvents of the antiseptic solution is compatible with the other components of the composition and is non-toxic when applied to human or animal skin. Suitable solvents include, but are not limited to water, alcohols, acetone, esters, chlorinated hydrocarbons and chlorofluorohydrocarbons. Preferably, the solvent of the antiseptic solution comprises a mixture of one or more lower alkanols and water, preferably deionized water. In a preferred embodiment, the solvent comprises water and about 20 to about 95% (v/v) of at least one $C_1$-$C_8$ lower alkanol such as, for example, isopropanol, ethanol and other alcohols. Preferably, the solvent comprises water and about 50 to about 90% (v/v) of at least one $C_1$-$C_8$ lower alkanols. The preferred lower alkanol is isopropanol. The preferred water is deionized water. In a preferred embodiment, the solvent of the antiseptic solution of the invention consists essentially of deionized water and about 70% (v/v) of isopropyl alcohol. Preferably the solvent of antiseptic solution of the invention is deionized water and 70% (v/v) of isopropyl alcohol.

Applicants have found that an antiseptic solution of the invention has good stability when the active ingredient di(4-chlorophenyldiguanido) compound of formula (I) or pharmaceutically acceptable salt thereof used to form the antiseptic solution of the invention, has a residual concentration of p-chloroaniline of less than about 500 ppm, preferably less than about 300 ppm, more preferably less than about 100 ppm, even more preferably less than about 50 ppm, and still even more preferably equal to or less than about 43 ppm, by HPLC. Additionally, good results are obtained when di(4-chlorophenyldiguanido) compound of formula (I) or pharmaceutically acceptable salt thereof, as used to form the antiseptic solution of the invention typically shows a total impurities content of less than about 0.1%, and preferably less than about 0.05%, as determined by HPLC.

In an embodiment, the present invention provides an antiseptic solution consisting of a pharmaceutically acceptable salt of di(4-chlorophenyldiguanido) compound of formula (I), one or more solvents, and one or more anionic dyes in an amount sufficient to stain a patient's skin or surgical field before surgery, wherein the solvent is an aqueous lower alcohol solution. In a preferred embodiment, the antiseptic solution consists of di(4-chlorophenyldiguanido) compound of formula (I) or pharmaceutically acceptable salt thereof, a mixture of isopropanol and water, and one or more anionic dyes in an amount sufficient to stain a patient's skin or surgical field before surgery. In a particularly preferred embodiment, the antiseptic solution consists of 2% (w/v) of di(4-chlorophenyldiguanido) compound of formula (I) digluconate, 70% (v/v) of isopropanol, water and one or more anionic dyes in an amount sufficient to stain a patient's skin or surgical field before surgery.

In a particular preferred embodiment, the invention provides a stable antiseptic solution comprising, consisting essentially of, or consisting of a di(4-chlorophenyldiguanido) compound of formula (I) or a pharmaceutically acceptable salt thereof, and one or more anionic dyes, wherein the anionic dye or the total amount of anionic dyes present in the antiseptic solution are sufficient to stain a patient's skin or surgical field before surgery, wherein the antiseptic solution is essentially free of any cationic excipient, wherein the concentration of the anionic dye is less than 5%, the di(4-chlorophenyldiguanido) compound of formula (I) or pharmaceutically acceptable salt thereof is present in an amount from 0.1 to 10% (w/v), wherein the solvent of the solution comprises a mixture of one or more lower alkanols and deionized water.

In a first preferred embodiment, the invention provides a stable antiseptic solution comprising about 30% (v/v) of water, about 70% (v/v) of isopropanol, about 2% (w/v) of a pharmaceutically acceptable salt of the di(4-chlorophenyldiguanido) compound of formula (I), preferably the gluconate salt, and about 0.025% (w/v) of an anionic dye. In a second preferred embodiment, the invention provides a stable antiseptic solution comprising about 30% (v/v) of water, about 70% (v/v) of isopropanol, about 2% (w/v) of a pharmaceutically acceptable salt of the di(4-chlorophenyldiguanido) compound of formula (I), preferably the gluconate salt, and about 0.2% (w/v) of an anionic dye.

Although the solution of the invention preferably comprises the excipients mentioned herein, and more preferably consists essentially of these excipients, one skilled in the art will recognize that it is possible to add further excipients which do not materially affect the invention. For example, non-ionic excipients can be added such as, for example, alcohols, alkanolamides (amides derived from alkanolamines, cocamide MEA, cocamide DEA, oleamide DEA, fatty acid diethanolamide of vegetable oils, ethoxylated amides, PEG-4-cocamide MEA amine oxides, esters (ethoxylated carboxylic acid-PEG-40-castor oil, ethoxylated glycerides, PEG-24-glyceryl stearate, glycol esters and derivatives, monoglycerides, polyglyceryl esters, esters and ethers of polyols, esters of sorbitan/sorbitol, triesters of phosphoric acid), ethers (ethoxylated alcohols, ceteareth-12, ceteareth-20, ceteareth-30, laureth-2, laureth-3, laureth-4, oleth-5, oleth-10, ethoxylated lanolin derivatives, polysiloxanes ethoxylated, propoxylated ethers of PEG-PPG-1-PEG-9-lauryl ether glycol).

The following abbreviations are used herein: monoethanolamine (MEA); diethanolamine DEA); polyethyleneglycol (PEG); and polypropyleneglycol (PPG).

The present invention further provides a processes of preparing the antiseptic solution described herein. Applicants have surprisingly found that when the antiseptic solution of the present invention is prepared by combining or adding the components in a particular manner (e.g., specific order), precipitation is avoided when compared to other processes. Surprisingly, the stability of the final antiseptic solution depends on the order in which the excipients are combined/mixed.

The process according to the present invention comprises, consists essentially of, or consists of (i) dissolving one or more anionic dyes in one or more first solvents to provide an anionic dye solution and (ii) adding the di(4-chlorophenyldiguanido) compound of formula (I) or the pharmaceutically acceptable salt thereof to the anionic dye solution of step (i).

In keeping with the invention, the di(4-chlorophenyldiguanido) compound of formula (I) or the pharmaceutically acceptable salt thereof can be added to the anionic dye solution in any suitable manner. In some embodiments, the di(4-chlorophenyldiguanido) compound of formula (I) or the pharmaceutically acceptable salt thereof is added to the anionic dye solution in solid form. Typically, the solid form of the di(4-chlorophenyldiguanido) compound of formula (I) is dispersed or dissolved in a solvent and then added to the anionic dye solution. In an embodiment, the di(4-chlorophenyldiguanido) compound of formula (I) or the pharmaceutically acceptable salt thereof is added to the anionic dye solution dispersed in a solvent. In a preferred embodiment, the di(4-chlorophenyldiguanido) compound of formula (I) or the pharmaceutically acceptable salt thereof is added to the anionic dye solution dissolved in a solvent The one or more first solvent typically is selected from the group consisting of one or more lower alkanols, water, and mixtures thereof.

In another embodiment, the invention provides a process for preparing a stable antiseptic solution comprising a di(4-chlorophenyldiguanido) compound of formula (I) or the pharmaceutically acceptable salt thereof comprising, consisting essentially of, or consisting of (i) dissolving one or more anionic dyes in one or more first solvents to provide an anionic dye solution, (ii) dissolving the di(4-chlorophenyldiguanido) compound of formula (I) or the pharmaceutically acceptable salt thereof in one or more second solvents to a provide a solution of a compound of formula (I) or a pharmaceutically acceptable salt thereof, and (iii) combining the anionic dye solution and solution of a compound of formula (I) or a pharmaceutically acceptable salt thereof.

In a preferred embodiment, the second solvent is selected from the group consisting of one or more lower alkanols, water, and mixtures thereof.

In keeping with an aspect of the inventive process, the anionic dye and/or the di(4-chlorophenyldiguanido) compound of formula (I) or the pharmaceutically acceptable salt thereof can be dissolved in water before use. Preferably, the anionic dye is dissolved in water or in mixtures comprising water, and the di(4-chlorophenyldiguanido) compound of formula (I) or the pharmaceutically acceptable salt thereof is dissolved in isopropanol or in mixtures comprising isopropanol.

In an embodiment, the inventive process comprises mixing the one or more anionic dyes with water to form a solution and adding one or more lower alkanols to the solution.

The stable antiseptic solution comprising a di(4-chlorophenyldiguanido) compound of formula (I) or a pharmaceutically acceptable salt thereof, and one or more anionic dyes, wherein the anionic dye or the total amount of anionic dyes present in the antiseptic solution are in an amount sufficient to stain a patient's skin or surgical field before surgery, wherein the antiseptic solution is essentially free of any cationic excipient, can be prepared by a process comprising the steps of (i) dissolving one or more anionic dyes in a portion of one more first solvents to provide an anionic dye solution, (ii) adding the di(4-chlorophenyldiguanido) compound of formula (I) or the pharmaceutically acceptable salt thereof and mixing until dissolution, and (iii) finally adding the rest of the amount of the one or more first solvents to the solution formed after adding the di(4-chlorophenyldiguanido) compound of formula (I) or the pharmaceutically acceptable salt thereof.

In an embodiment, the invention provides a process for preparing an antiseptic solution comprising the steps of (i) dissolving one or more anionic dyes in a portion of one or more first solvents to provide an anionic dye solution, (ii) adding to the anionic dye solution the di(4-chlorophenyldiguanido) compound of formula (I) or pharmaceutically acceptable salt thereof previously dissolved in a solvent and mixing until complete dissolution, and finally adding the remaining portion of the one or more first solvents.

In the process according to the present invention, the portion of solvent added to the anionic dye is typically at least 15% (v/v) of the required amount of solvent, preferably at least 30% (v/v), more preferred at least 50% (v/v), most preferred 80-90% (v/v), and still most preferred about 80% (v/v).

In keeping with the invention, the above solvents used can be the same or they can be different solvents. However, if the solvent in the step where the anionic dye is dissolved is only water, the di(4-chlorophenyldiguanido) compound of formula (I) or pharmaceutically acceptable salt thereof, is added dissolved in a solvent which is not only water. If the solvent in the step where the anionic dye is dissolved is a mixture of water and isopropanol, the di(4-chlorophenyldiguanido) compound of formula (I) or pharmaceutically acceptable salt thereof, is added dissolved in a solvent which is only isopropanol, or only water or a mixture of isopropanol with water. Also preferably the first solvent in the step where the anionic dye anion is dissolved is never only isopropanol.

It is preferred that a process according to the present invention comprises the steps of dissolving one or more anionic dyes in deionized water, preferably deionized water to provide an anionic dye solution, then adding a portion of the amount of a $C_2$-$C_8$ lower alkanol, preferably isopropanol, then adding di(4-chlorophenyldiguanido) compound of formula (I) or a pharmaceutically acceptable salt thereof previously dissolved in water and mixing until complete dissolution, and finally adding the rest of the amount of the $C_2$-$C_8$ lower alkanol, preferably isopropanol.

Without wishing to be bound to a particular theory, it is believed that one or more complexes form between the components of the antiseptic solution (e.g., one or more anionic dyes, di(4-chlorophenyldiguanido) compound of formula (I) or pharmaceutically acceptable salt, and one or more solvents) which facilitate the chemical and physical stability of the compositions. For example, it is thought that the anionic dye forms a complex with solvent molecules when the anionic dye is dissolved in one or more first solvents, particularly when the first solvent comprises water or is water. Further, it is thought that the anionic dye-solvent complex is dispersed and is surrounded by a second solvent, when present, particularly when the second solvent comprises a $C_2$-$C_8$ lower alkanol or is a $C_2$-$C_8$ lower alkanol. It is also believed that the di(4-chlorophenyldiguanido) compound of formula (I) or pharmaceutically acceptable salt thereof forms a complex with the anionic dye complex, particularly if the di(4-chlorophenyldiguanido) compound of formula (I) or pharmaceutically acceptable salt thereof is added dispersed in a solvent (e.g., water), particularly in the presence of a $C_2$-$C_8$ lower alkanol. Complex formation occurs between the two systems due to the difference in solvent polarity that reaches stable state and ensures that the antiseptic solution of the present invention is chemically and physically stable and without precipitation or particle formation.

According to a further embodiment of the present invention, compound of formula (I) or a pharmaceutically acceptable salt thereof is separated in the stable antiseptic solution from the anionic dye by at least two solvents of different polarity. For example, the compound of formula (I) is essentially surrounded by one solvent and the anionic dye is essentially surrounded by the other solvent of different polarity.

It is further advantageous to prepare an antiseptic solution of the present invention under an inert atmosphere to help preserve the chemical and physical stability of the antiseptic solution. For example, the antiseptic solutions of the invention can be prepared under an inert gas atmosphere (e.g., nitrogen or argon gas). The skilled artisan will recognize that other variations are suitable.

In a further embodiment, the invention provides a process for preparing a stable antiseptic solution comprising, consisting essentially of, or consisting of the steps of dissolving one or more anionic dyes in one or more first solvents to provide an anionic dye solution and adding the di(4-chlorophenyldiguanido) compound of formula (I) or the pharmaceutically acceptable salt thereof to the anionic dye solution and mixing until dissolution.

The anionic dye and/or the di(4-chlorophenyldiguanido) compound of formula (I) or the pharmaceutically acceptable salt thereof, before use can be dissolved in water, preferably deionized water.

In another embodiment, the invention provides a process of preparing a stable antiseptic solution comprising a di(4-chlorophenyldiguanido) compound of formula (I), one or more anionic dyes, wherein the total amount of anionic dye present in the antiseptic solution is in an amount sufficient to stain a patient's skin or surgical field when applied before surgery, and wherein the antiseptic solution is essentially free of any cationic excipient, and is produced by a process comprising the steps of dissolving one or more anionic dyes in one or more first solvents to provide an anionic dye solution and adding the di(4-chlorophenyldiguanido) compound of formula (I) or the pharmaceutically acceptable salt thereof to the anionic dye solution and mixing until dissolution.

Additionally, the process of the present invention may also comprise additional steps, for example, a final addition of more solvent.

In a preferred embodiment, the first solvent comprises one or more solvents. The first solvent can comprise water or a mixture of water with one or more lower alkanols. The preferred lower alkanols are methanol, ethanol, propanol, isopropanol, butanol, pentanol, and mixtures thereof. In a particular preferred embodiment, the lower alkanol is isopropanol.

In keeping with an aspect of the invention, the step of providing an anionic dye solution can be divided into substeps. For example, in an embodiment the step of providing an anionic dye further comprises the steps of mixing the one or more anionic dyes with water to form a solution and adding one or more lower alkanols to the said solution. In a preferred embodiment, the lower alkanol is isopropanol.

When mixtures of water with one or more lower alkanols are used as a first solvent, the ratio of water to lower alkanol is at least about 1:1 (v/v), that is, the amount of water in volume is equal to or greater than the amount of lower alkanol in volume. In a preferred embodiment, the ratio of water to lower alkanol is at least about 2:1 (v/v), even more preferably at least about 4:1 (v/v), still more preferably at least 8:1 (v/v), and most preferred the ratio of water and lower alkanol is at least about 10:1 (v/v).

In a preferred embodiment the first solvent comprises more than 50% (v/v) of water. More preferably, the first solvent comprises more than 80% (v/v) of water. Most preferred, the first solvent is water.

In another preferred embodiment, the first solvent is a mixture of water and isopropanol.

The addition of the di(4-chlorophenyldiguanido) compound of formula (I) or pharmaceutically acceptable salt thereof, in step (ii) can be done in various ways. For example, the compound of formula (I) can be added in solid form, dispersed in a solvent or dissolved in a solution of one or more second solvents. Preferably the di(4-chlorophenyldiguanido) compound of formula (I) or pharmaceutically acceptable salt thereof, is added dissolved in one or more second solvents. Desirably, the anionic dye solution is stirred during the addition of the di(4-chlorophenyldiguanido) compound of formula (I) or pharmaceutically acceptable salt thereof, regardless of the manner in which the compound of formula (I) is added.

Just as the first solvent, the second solvent can comprise one or more solvents. The second solvent can comprise water, one or more lower alkanols, or a mixture thereof. The preferred lower alkanol of the second solvent is methanol, ethanol, propanol, isopropanol, butanol, pentanol, and mixtures thereof. Preferably, the second solvent comprises isopropanol.

In a preferred embodiment, the second solvent is water, methanol, ethanol, propanol, isopropanol, butanol, pentanol or any mixture thereof, preferably is water, isopropanol or water and isopropanol.

The second solvent can comprise a suitable amount of one or more lower alkanols. Preferably, the second solvent comprises more than 50% (v/v) of the total volume of the second solvent one or more lower alkanols, more preferably more than 80% (v/v) of one or more lower alkanols. In an even more preferred embodiment the second solvent is one or more lower alkanols. In a particularly preferred embodiment, the second solvent is isopropanol.

It is desirable that the first solvent comprises a suitable amount of water and that the second solvent comprises a suitable amount of one or more lower alkanols. In a preferred embodiment, the first solvent comprises more than about 50% (v/v) of water, and the second solvent comprises more than 50% (v/v) of one or more lower alkanols. Even more preferably, the first solvent comprises more than 80% (v/v) of water and the second solvent comprises more than 80% (v/v) of one or more lower alkanols. Preferably, when the solvent for the anionic dye solution is only water, then the one or more second solvents comprise one or more lower alkanols (i.e., the second solvent is not only water). In addition, when the solvent for the anionic dye solution is isopropanol, then the second solvent is not only isopropanol.

In a preferred embodiment, the first solvent is water and the second solvent is a mixture of isopropanol and water.

In a preferred embodiment, the first solvent is water and the second solvent is isopropanol.

In a preferred embodiment, the first solvent is a mixture of water and isopropanol and the second solvent is isopropanol.

In a preferred embodiment, the first solvent is a mixture of water and isopropanol and the second solvent is another mixture of water and isopropanol.

In a preferred embodiment, the first solvent is a mixture of water and isopropanol and the second solvent is water.

In a particularly preferred embodiment, the inventive process provides an antiseptic solution comprising about 30% (v/v) of water, about 70% (v/v) of isopropanol, about 2% (w/v) of a pharmaceutically acceptable salt of the di(4-chlorophenyldiguanido) compound of formula (I), preferably the gluconate salt, and about 0.025% (w/v) of an anionic dye. In an alternative embodiment, the inventive process provides an antiseptic solution comprising about 30% (v/v) of water, about 70% (v/v) of isopropanol, about 2% (w/v) of a pharmaceutically acceptable salt of the di(4-chlorophenyldiguanido) compound of formula (I), preferably the gluconate salt, and about 0.2% (w/v) of an anionic dye.

Another advantage is that the inventive process can be conducted at mild temperatures. For example, the anionic dye solution can be formed at a temperature below 60° C., preferably at a temperature below 40° C. In addition, the addition of the di(4-chlorophenyldiguanido) compound of formula (I) can be conducted at a temperature below 60° C., preferably at a temperature below 40° C.

In keeping with an aspect of the invention the additions of solvents during the inventive process can be made in a portion wise manner. For example, the anionic dye solution can be prepared such that only a portion of the first solvent is added during the early steps of the process. Accordingly, at a later time during the process the balance of the one or more first solvents can then be added. This is further illustrated as described herein.

In an embodiment, the invention provides a process for preparing a stable antiseptic solution comprising di(4-chlorophenyldiguanido) compound of formula (I) digluconate comprising the steps of (i) dissolving one or more anionic dyes in one or more first solvents to provide an anionic dye solution, (ii) adding one or more lower alkanols to the anionic dye solution, (iii) dissolving the di(4-chlorophenyldiguanido) compound of formula (I) digluconate in one or more second solvents to provide a solution of di(4-chlorophenyldiguanido) compound of formula (I) digluconate, (iv) combining the anionic dye solution and the solution of step (iii) to provide a combined solution, and (v) adding one or more lower alkanols to the combined solution of step (iv).

The invention also provides a stable antiseptic solution comprising a di(4-chlorophenyldiguanido) compound of formula (I) or a pharmaceutically acceptable salt thereof, one or more anionic dyes, wherein the anionic dye or the total amount of anionic dyes present in the antiseptic solution are in an amount sufficient to stain a patient's skin or surgical field before surgery, wherein the antiseptic solution is essentially free of any cationic excipient, and can be produced by a process comprising the steps of dissolving one or more anionic dyes mixing until dissolution, first one or more anionic dye with the part of the amount of solvent; after mixing until dissolution one or more anionic dye with the part of the amount of solvent, adding the di(4-chlorophenyldiguanido) compound of formula (I) or the pharmaceutically acceptable salt thereof and mixing until dissolution; and finally adding the rest of the amount of the specific solvent to the solution formed after dissolving the di(4-chlorophenyldiguanido) compound of formula (I) or the pharmaceutically acceptable salt thereof.

In a preferred embodiment, the antiseptic solution comprising di(4-chlorophenyldiguanido) compound of formula (I) or pharmaceutically acceptable salt thereof and an anionic dye in an amount sufficient to stain a patient's skin or surgical field before surgery, is obtainable by the process that comprises the steps of dissolving one or more anionic dyes in water until complete dissolution, then adding a part of the amount of $C_2$-$C_8$ lower alkanol, preferably isopropanol, then adding di(4-chlorophenyldiguanido) compound of formula (I) or pharmaceutically acceptable salt thereof and mixing until complete dissolution, and finally adding the rest of the amount of the $C_2$-$C_8$ lower alkanol, preferably isopropanol.

In a further particularly preferred embodiment, the antiseptic solution comprising di(4-chlorophenyldiguanido) compound of formula (I) digluconate thereof and FD&C Red No. 40 (Allura Red) anionic dye in an amount sufficient to stain a patient's skin or surgical field before surgery is obtainable by the process that comprises the steps of dissolving FD&C Red No. 40 (Allura Red) anionic dye in water until complete dissolution, and then adding 80% of the amount of isopropanol, then adding di(4-chlorophenyldiguanido) compound of formula (I) digluconate and mixing until complete dissolution, and finally adding the rest of the amount of isopropanol.

In a preferred embodiment, the present invention provides a stable antiseptic solution comprising a di(4-chlorophenyldiguanido) compound of formula (I) or a pharmaceutically acceptable salt thereof and one or more anionic dyes, wherein the anionic dye or the total amount of anionic dyes present in the antiseptic solution is between about 0.05% (w/v) and about 1.0% (w/v), and wherein the solution does not contain cationic excipients, and wherein said antiseptic solution is produced by a process comprising the steps of (i) dissolving one or more anionic dyes in a solvent selected from the group consisting of water, isopropanol, and mixtures thereof and (ii) adding the gluconate salt of the di(4-chlorophenyldiguanido) compound of formula (I), wherein the gluconate salt of compound of formula (I) is dissolved in a solvent selected from the group consisting of water, isopropanol, and mixtures thereof, provided that if the first solvent in step (i) is only water the second solvent in step (ii) is not only water, or if the first solvent in step (i) is a mixture of water and isopropanol the second solvent in step (ii) is only isopropanol, or only water or a mixture of isopropanol with water. The first solvent in step (i) is never only only isopropanol.

An antiseptic solution as provided by the present invention is a disinfectant suitable for any purpose related to its antiseptic and/or disinfectant properties. For example, the inventive compositions can be used to prevent infections, including but not limited to, nosocomial infections, surgical-site infections, catheter-related infections, surgical wound infections, and oral infections. In addition, the antiseptic solutions of the invention can be used in, for example, skin disinfection; handwashing; oral care; irrigation of surgical wounds, the urinary bladder or vagina; the topical treatment of burn wounds; and the treatment of peritonitis in peritoneal dialysis.

EXAMPLES

The following examples further illustrate the invention but, of course, should not be construed as in any way limiting its scope.

Amounts are reported in weight-volume percent, unless otherwise indicated. The stability tests were performed as described herein, unless otherwise noted.

Example 1

This example demonstrates stable antiseptic solutions of the invention, the components of which are listed in Table 1 and Table 2. Examples 1A-1D contained chlorhexidine digluconate added as a solid and example 1E contained chlorhexidine digluconate added as a 20% aqueous solution. Examples 1A-1D contained FD&C Red No. 40 as the anionic dye and example 1E contained Food Red 3 Camoisina as the anionic dye. The antiseptic solutions contained isopropyl alcohol (1A), (1B) and 1D, 99% ethyl alcohol (1C), or 70% ethyl alcohol (1E) as the lower alkanols.

TABLE 1

| Component | Ex. 1A | Ex. 1B | Ex. 1C | Ex. 1D |
|---|---|---|---|---|
| | Amount (% w/v or v/v) | | | |
| chlorhexidine digluconate (w/v) | 2 | 2 | 2 | 2 |
| anionic dye FD&C Red No. 40 (Allura Red) (w/v) | 0.2 | 0.45 | 0.2 | 0.025 |
| isopropyl alcohol (v/v) | 70 | 70 | — | 70 |
| ethyl alcohol, 99% (v/v) | — | — | 70 | — |
| deionized water | qsp 100 mL | qsp 100 mL | qsp 100 mL | qsp 100 mL |

TABLE 2

| Component | Ex. 1E Amount |
|---|---|
| chlorhexidine digluconate, 20% v/w, aq. solution | 1 mL |
| anionic dye Food Red 3 Camoisina | 0.07% (w/v) |
| ethyl alcohol, 70% | qsp 100 mL |

Antiseptic solutions 1A-1E were prepared as follows: anionic dye FD&C Red No. 40 (Allura Red) was dissolved in deionized water (Examples 1A-1D) and anionic dye Food Red 3 Carmoisine was dissolved in ethanol (Example 1E). The mixtures were stirred with a magnetic stirrer until dissolution was complete at room temperature. 80% of theoretical weight of isopropanol (Examples 1A, 1B and 1D) and ethanol (Examples 1C and 1E) was added to the above solution and stirred with magnetic stirrer until complete homogenity for 10 minutes at room temperature. Chlorhexidine digluconate 20% v/w aqueous solution was weighed and added to the solutions in Examples IA to 1E. The mixture was stirred with magnetic stirrer until complete homogeneity for 10 minutes at room temperature. The remaining portion of isopropanol (Examples 1A, 1B and 1D) and ethanol (Examples 1C and 1E) was added, and the mixture was stirred with magnetic stirrer for another 10 minutes at room temperature. The pH and density of the resulting solution were measured. The solution was filtered through clarificant filter of 100 μm filters and filled in plastic high density polyethylene (HDPE) vials.

Example 2

This example demonstrates the stability of antiseptic solutions of the invention. The stability of the antiseptic solutions of Example 1 was evaluated at 0, 3, and 6 months using the following conditions: 25±2° C. & 60%±5% relative humidity (Table 3), or 40±2° C. & 75%±5% relative humidity (Table 4). The visual appearance of the solutions was monitored for the presence of particles. The concentration of p-chloroaniline impurity was evaluated as described herein.

The results are set forth in Table 3 and Table 4.

TABLE 3

| | | | | p-Chloroaniline [NMT 0.25%] | | |
|---|---|---|---|---|---|---|
| | Appearance (free of particles) | | | 0 | 3 | 6 |
| Comp. | 0 months | 3 months | 6 months | months | months | months |
| Ex. 1A | conforms | conforms | conforms | 0.01% | 0.02% | 0.02% |
| Ex. 1B | conforms | conforms | conforms | 0.01% | 0.01% | 0.02% |
| Ex. 1C | conforms | conforms | conforms | 0.02% | 0.04% | 0.08% |
| Ex. 1D | conforms | — | — | 0.02% | — | — |
| Ex. 1E | conforms | conforms | conforms | 0.02% | not tested | 0.06% |

TABLE 4

| | | | | p-Chloroaniline [NMT 0.25%] | | |
|---|---|---|---|---|---|---|
| | Appearance (free of particles) | | | 0 | 3 | 6 |
| Comp. | 0 months | 3 months | 6 months | months | months | months |
| Ex. 1A | conforms | conforms | conforms | 0.01% | 0.06% | 0.14% |
| Ex. 1B | conforms | conforms | conforms | 0.01% | 0.08% | 0.12% |

As is apparent by the data set forth in Table 3 and Table 4, antiseptic solutions containing chlorhexidine digluconate, FD&C Red No. 40 or Food Red 3 Camoisina, a lower alkanol, and water in accordance with the invention have good chemical and physical stability properties.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A stable ready for administration, colored antiseptic solution comprising from 1% to 3% (w/v) of a di(4-chlorophenyldiguanido) compound of formula (I) or a pharmaceutically acceptable salt thereof,

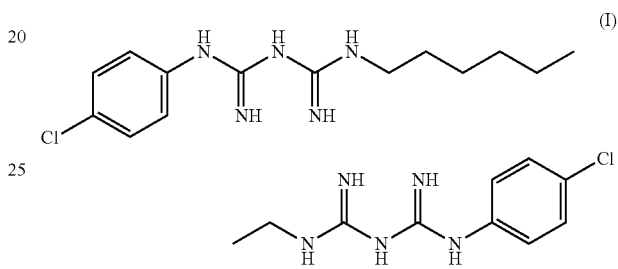

about 0.01% to about 0.04% (w/v) of one or more anionic dyes present in an amount sufficient to stain a patient's skin or surgical field, water, and about 70% (v/v) alkanol selected from the group consisting of isopropanol and mixtures of isopropanol/ethanol, wherein the antiseptic solution contains less than 0.01% by weight of cationic excipients, and the antiseptic solution is stable and contains less than about 0.25% (w/w) p-chloroaniline for at least about 6 months at 25±2° C. and 60%±5% relative humidity, or 40±2° C. and 75%±5% relative humidity.

2. The stable ready for administration, colored antiseptic solution according to claim 1, wherein the solution is stable for at least about 12 months at 25±2° C. and 60%±5% relative humidity, or 40±2° C. and 75%±5% relative humidity.

3. The stable ready for administration, colored antiseptic solution according to claim 1, wherein the solution is stable for at least about 18 months at 25±2° C. and 60%±5% relative humidity, or 40±2° C. and 75%+5% relative humidity.

4. The stable ready for administration, colored antiseptic solution according to claim 1, wherein the solution contains less than about 0.15% p-chloroaniline for at least about 6 months at 25±2° C. and 60%±5% relative humidity or 40±2° C. and 75%±5% relative humidity.

5. The stable ready for administration, antiseptic solution according to claim 1, wherein the compound of formula (I) is N,N"-bis(4-chlorophenyl)-3,12-diimino-2,4,11,13-tetraazatetradecanediimidamide digluconate.

6. A stable ready for administration, colored antiseptic solution comprising about 2% (w/v) of a pharmaceutically acceptable salt of a di(4-chlorophenyldiguanido) compound of formula (I):

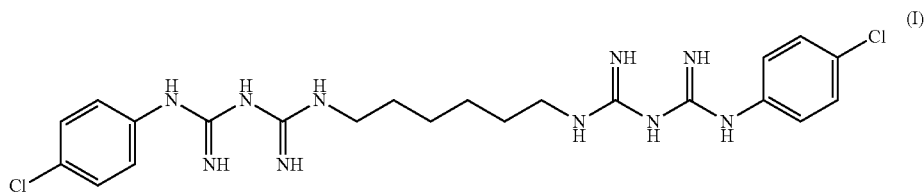 [SMILES: N=C(NCCCCCCNC(=N)NC(=N)Nc1ccc(Cl)cc1)NC(=N)Nc1ccc(Cl)cc1]

water and about 70% (v/v) isopropanol, and about 0.01% to about 0.04% (w/v) of anionic dye, wherein the antiseptic solution contains less than 0.01% by weight of cationic excipients, and the stable antiseptic solution is stable and contains less than about 0.25% (w/w) p-chloroaniline for at least about 6 months at 25±2° C. and 60%±5% relative humidity, or 40±2° C. and 75%±5% relative humidity.

7. The antiseptic solution according to claim 6, wherein the compound of formula (I) is N,N''-bis(4-chlorophenyl)-3,12-diimino-2,4,11,13-tetraazatetradecanediimidamide digluconate.

8. A stable, colored antiseptic solution comprising from 1% to 3% (w/v) of a di(4-chlorophenyldiguanido) compound of formula (I) or a pharmaceutically acceptable salt thereof, less than 0.5% (w/v) of one or more anionic dyes present in an amount sufficient to stain a patient's skin or surgical field, water, and about 70% (v/v) alkanol selected from the group consisting of ethanol, isopropanol, and mixtures thereof, wherein the stable, colored antiseptic solution is prepared by (i) dissolving one or more anionic dyes in one or more first solvents to provide an anionic dye solution, comprising water and optionally further comprising an alkanol selected from the group consisting of ethanol, isopropanol, and mixtures thereof, (ii) adding ethanol, isopropanol, or mixtures thereof to the anionic dye solution, (iii) dissolving the di(4-chlorophenyldiguanido) compound of formula (I) digluconate in one or more second solvents selected from the group consisting of ethanol, isopropanol, water, and mixtures thereof, to provide a solution of di(4-chlorophenyldiguanido) compound of formula (I) digluconate, (iv) combining the anionic dye solution of step (ii) and the solution of step (iii) to provide a combined solution, and (v) adding ethanol, isopropanol, or mixtures thereof to the combined solution of step (iv) to obtain a stable antiseptic solution comprising water and about 70% (v/v) alkanol selected from the group consisting of ethanol, isopropanol, and mixtures thereof, wherein the antiseptic solution contains less than 0.01% by weight of cationic excipients, and the antiseptic solution is stable for and contains less than about 0.25% (w/w) p-chloroaniline for at least about 6 months at 25±2° C. and 60%±5% relative humidity, or 40±2° C. and 75%±5% relative humidity.

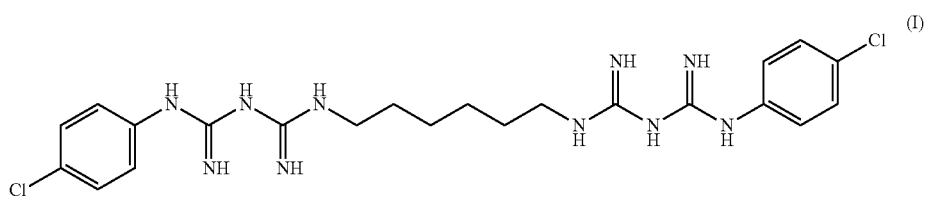 [SMILES: N=C(NCCCCCCNC(=N)NC(=N)Nc1ccc(Cl)cc1)NC(=N)Nc1ccc(Cl)cc1]

9. A process for preparing a stable antiseptic solution comprising from about 1% to about 3% (w/v) di(4-chlorophenyldiguanido) compound of formula (I) digluconate:

comprising:

(i) dissolving one or more anionic dyes in one or more first solvents to provide an anionic dye solution, comprising water and optionally further comprising an alkanol selected from the group consisting of ethanol, isopropanol, and mixtures thereof, (ii) adding ethanol, isopropanol, or mixtures thereof to the anionic dye solution, (iii) dissolving the di(4-chlorophenyldiguanido) compound of formula (I) digluconate in one or more second solvents selected from the group consisting of ethanol, isopropanol, water, and mixtures thereof, to provide a solution of di(4-chlorophenyldiguanido) compound of formula (I) digluconate, (iv) combining the anionic dye solution of step (ii) and the solution of step (iii) to provide a combined solution, and (v) adding ethanol, isopropanol, or mixtures thereof to the combined solution of step (iv) to obtain a stable antiseptic solution comprising water and about 70% (v/v) alkanol selected from the group consisting of ethanol, isopropanol, and mixtures thereof, wherein the antiseptic solution contains less than 0.01% by weight of cationic excipients, and the stable antiseptic solution is stable and contains less than about 0.25% (w/w) p-chloroaniline for at least about 6 months at 25±2° C. and 60%±5% relative humidity, or 40±2° C. and 75%±5% relative humidity.

* * * * *